(12) United States Patent
Migyanka

(10) Patent No.: US 7,597,494 B2
(45) Date of Patent: Oct. 6, 2009

(54) RETRACTABLE SELF CONTAINED TOPICAL SOLUTION SELF APPLICATION SYSTEM

(76) Inventor: Anthony George Migyanka, 645 Cowboys Pkwy., #3057, Irving, TX (US) 75063

(*) Notice: Subject to any disclaimer, the term of this patent is extended or adjusted under 35 U.S.C. 154(b) by 0 days.

(21) Appl. No.: 11/999,137

(22) Filed: Dec. 4, 2007

(65) Prior Publication Data

US 2009/0142119 A1    Jun. 4, 2009

(51) Int. Cl.
*A46B 5/02* (2006.01)
(52) U.S. Cl. .............................. 401/9; 401/6; 242/588.3
(58) Field of Classification Search .................. 401/6, 401/9, 131; 33/413, 414, 392; 239/52; 242/378, 242/378.1, 378.2, 588, 588.3, 588.6, 402, 242/405, 407
See application file for complete search history.

(56) References Cited

U.S. PATENT DOCUMENTS

| 1,208,068 | A | * | 12/1916 | Winchell ..................... 33/414 |
| 4,964,744 | A | * | 10/1990 | Whitear ......................... 401/6 |
| 5,013,171 | A | * | 5/1991 | Almond, II .................... 401/6 |
| 6,470,619 | B1 | * | 10/2002 | Snyder et al. .................... 43/1 |
| 6,745,485 | B2 | * | 6/2004 | Shor ........................... 33/414 |
| 6,899,481 | B2 | * | 5/2005 | Katsandres et al. ............ 401/6 |

* cited by examiner

*Primary Examiner*—David J Walczak
(74) *Attorney, Agent, or Firm*—Jeffrey Roddy

(57) ABSTRACT

A device for applying a lotion or fluid medicament to those areas of the human body difficult to access having a cable of adsorbent material spooled about an axle inside a fluid filled container with an annular orifice, and where the cable is pulled through the orifice carrying with it a measured amount of lotion for deposition and spreading upon the body. The axle is actuated by a dial extending above the surface of the fluid filled container whereby the user can rewind the cable by turning the dial.

11 Claims, 3 Drawing Sheets

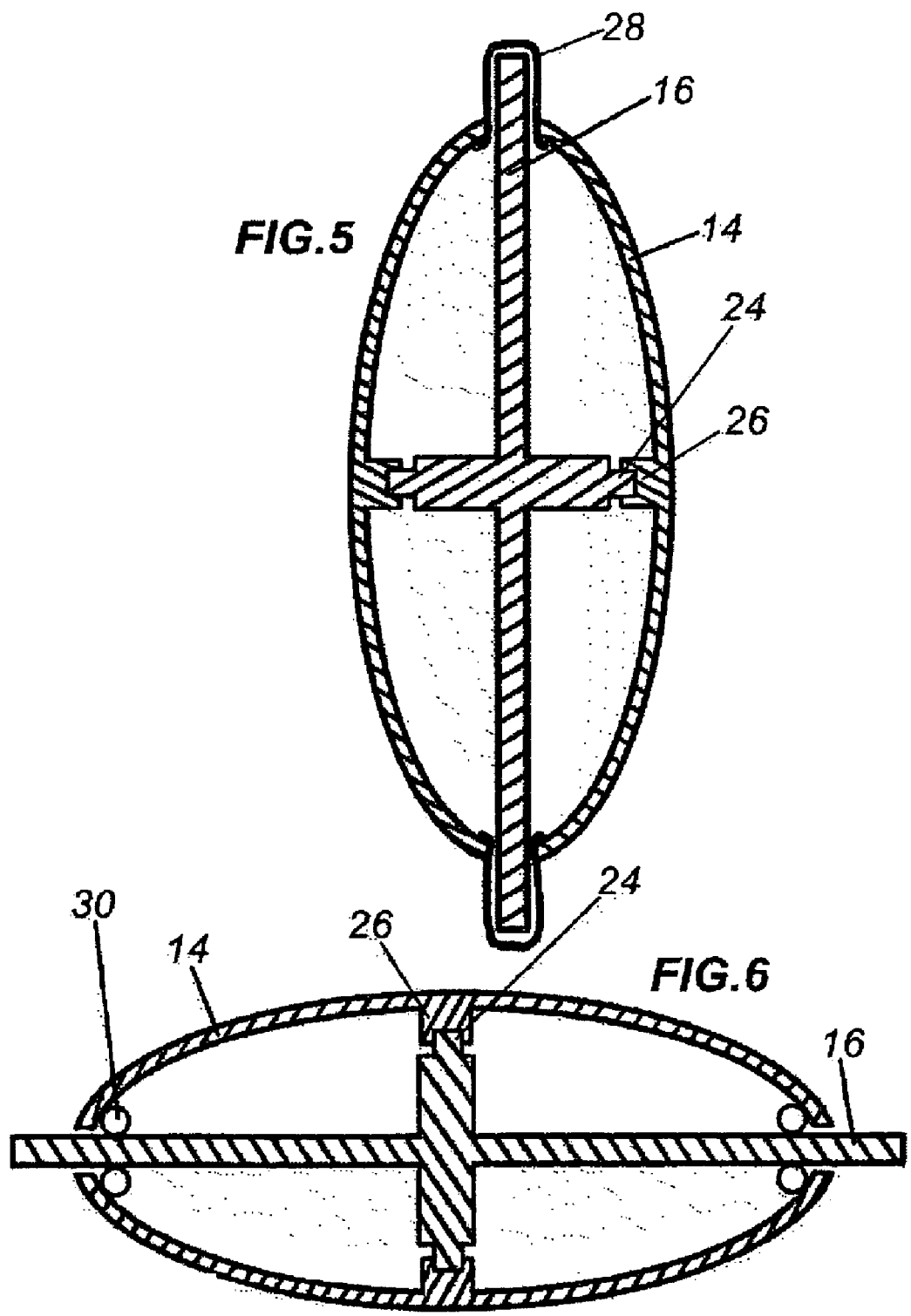

RETRACTABLE SELF CONTAINED TOPICAL SOLUTION SELF APPLICATION SYSTEM

CROSS REFERENCE TO RELATED APPLICATIONS

Not applicable

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISC

Not applicable

BACKGROUND OF THE INVENTION

A persistent problem exists in the solo application of a lotion, medicament, or sun screen to one's own body. Without the assistance of an aid or partner, several areas of the body may go untreated because of the inability of the individual to adequately reach those areas difficult for a person of normal range of motion, and practically impossible for the motion impaired. The elderly are especially vulnerable in this case, as many live alone and cannot obtain ready assistance. While the simple inaccessibility of many areas of the body is a problem in its own right, a related problem is the product waste that accompanies a clumsy effort of application. An expensive prescription lotion may be quickly wasted in attempts to apply it to difficult to reach areas resulting in an unevenness of product application which can have a negative impact on one's health and healthcare budget.

One patent, U.S. Pat. No. 6,341,910 (Kuehne), attempts to resolve this issue by having an elastic absorbent tether extending through a side opening of a cap where the cap is intended to be affixed to a lotion container. Although it is possible that such a device can work, the position of the tether at the side of the cap may be problematic as lotion is likely to accumulate at some point and run down the side of the container. It is also unclear what type of absorbent elastic material is intended, whether it may be extended to a practical length and whether it is possible to carry an adequate amount of lotion to the body surface.

BRIEF SUMMARY OF THE INVENTION

The present invention is a device for the self application of lotion or a fluid medicament to the surface of the human body. Difficult to reach spots such as the back and behind the legs can be accessed readily by the adsorbent cable applicator which resides in a ready state wound about an internal axle within the cavity of a fluid filled container. The container has an affixed cap with an annular orifice opening into the internal cavity with the cable extending therethrough so that it may be pulled out of the cavity by spooling. The adsorbent cable carries a measured amount of fluid with it, with the excess being removed by a restriction within the annular orifice. Once a sufficient length of cable is obtained, the cable is retained from further withdrawal from the container by restricting disc movement, whereupon the cable is placed at the desired area of the body and moved in an up and down motion to evenly distribute the fluid or lotion. After application is complete, the cable is retracted by rotating the disc and rewinding the cable.

The cable itself can be of elastic or non elastic material such as a polyester filament which is adsorbent and readily adheres to lotions. Simple friction may remove the lotion from the cable.

An object of the present invention is to provide a means for the easy self application of a lotion or medicament to those more inaccessible parts of the human body such as the back, especially for those individuals with restricted range of motion such as the disabled or elderly.

Another object of the present invention is to provide a means for applying a carefully measured amount to lotion or medicament to the surface of the human body without waste.

A further object of the present invention is to provide a means for evenly distributing lotion or medicament over the human body.

The applicant is not aware of any previously described art having the features and advantages of the present invention.

Other objects and advantages of the present invention will become apparent from the following descriptions, taken in connection with the accompanying drawings, wherein by way of illustration and example, a preferred embodiment of the present invention is disclosed.

BRIEF DESCRIPTION OF SEVERAL VIEWS OF THE DRAWINGS

FIG. 5 shows a sectional view of one embodiment of the present invention with the retractable cable omitted for clarity taken along lines 6'-6' of FIG. 3 showing the disc sheaths over those portions of the disc extending through slots of the container;

FIG. 6 shows a sectional view of one embodiment of the present invention with the retractable cable omitted for clarity taken along lines 6'-6' of FIG. 3 where disc seals replace the disc sheath as a means to retain internal fluid;

DETAILED DESCRIPTION OF THE INVENTION

Figure 1:
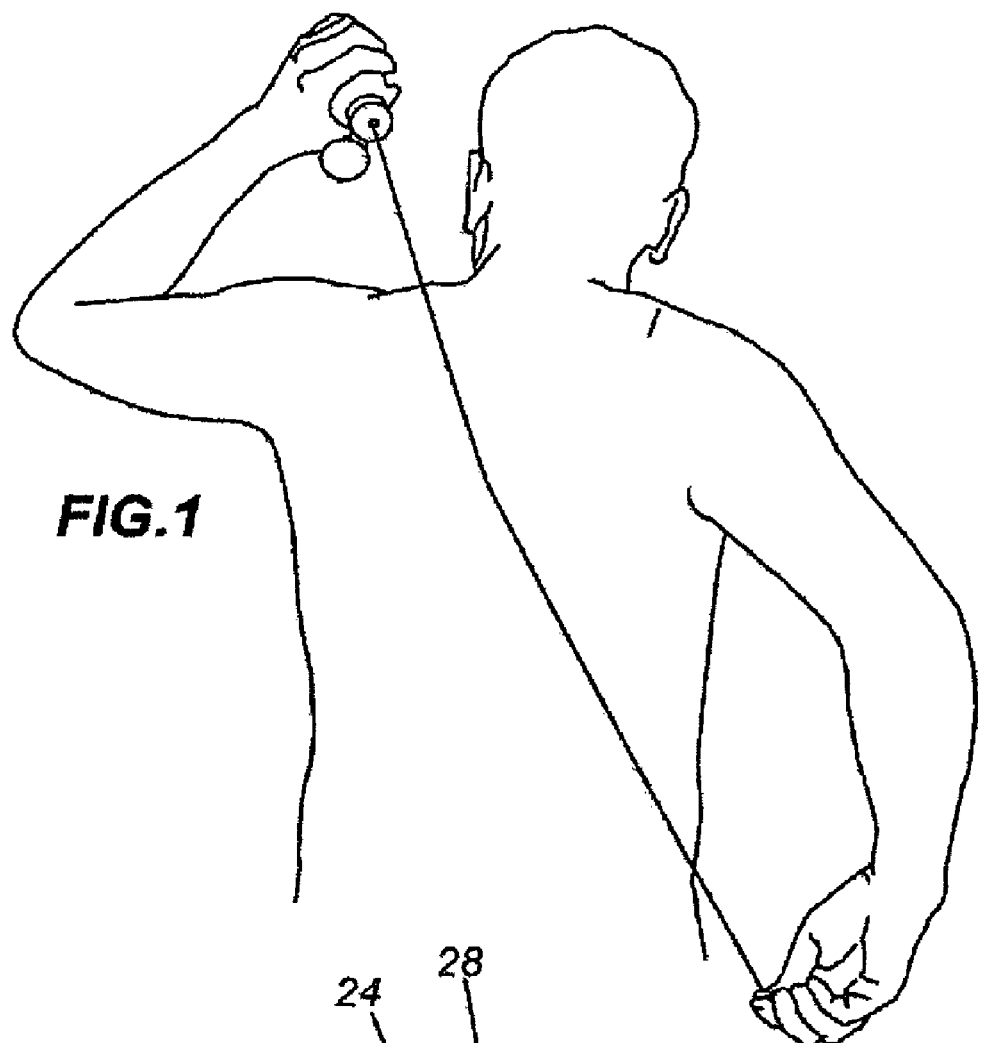
FIG. 1 is a perspective view of the present invention in typical use being used to applying lotion to ones back.

FIG. 1 Illustrates a perspective view of the present invention being used by an individual to apply a lotion or fluid medicament to the back. Spreading the lotion is accomplished by a back and forth motion.

Figure 2:
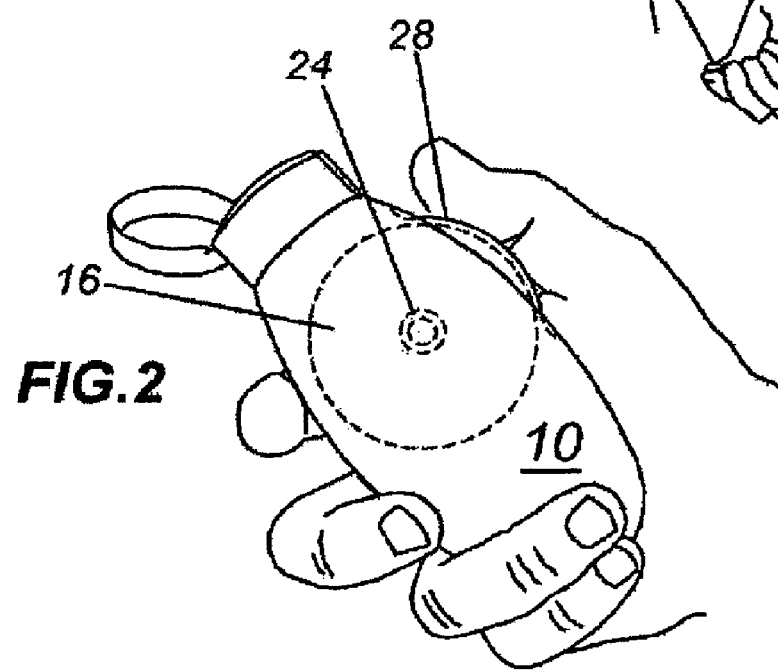
FIG. 2 is a perspective view of the present invention in typical use held by the hand with between thumb and forefinger with rotatable disc partially extending through one slot in the container body and a portion of the rotatable disc being covered by a flexible sheath, the axle retainers omitted for clarity.

FIG. 2 Illustrates a perspective view of the present invention 10 held in the hand between the thumb and forefinger.

Figure 3:
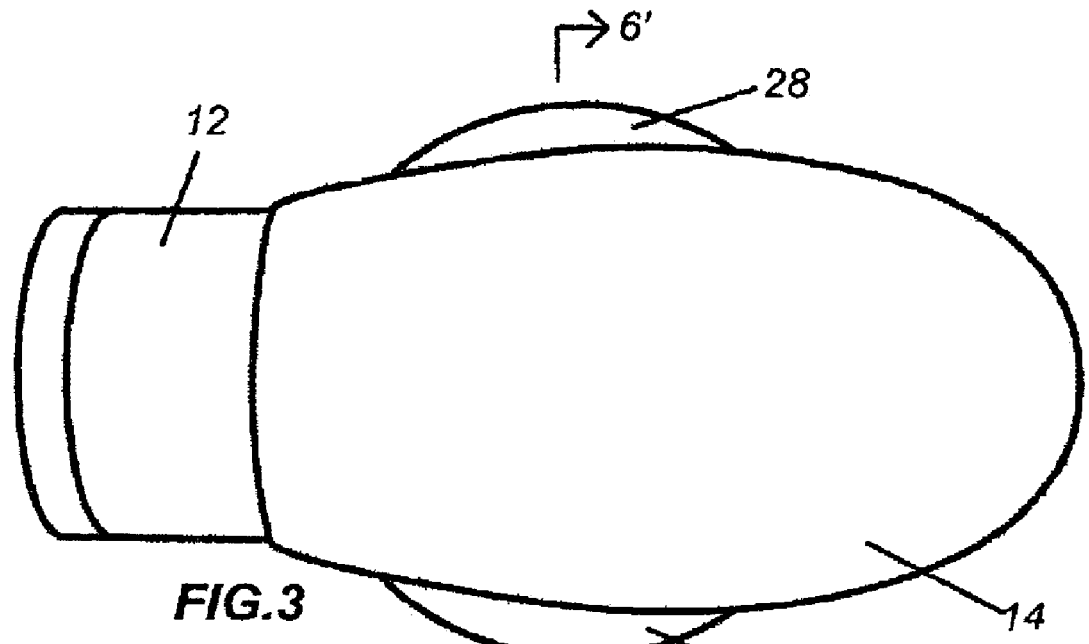
FIG. 3 is a plan view of the present invention showing the annular orifice of the cap with adsorbent cable extending therethrough with the flip to portion of the cap 12 closed.

FIG. 3 illustrates a perspective view of the present invention showing the container 14, the cap 12, and the annular orifice 22 from which extends the distal end of the cable 18 with its terminus affixed to a tab 20. Also shown is a portion of disc 16 passing through a slot in the container body and extending above the surface.

Figure 4:
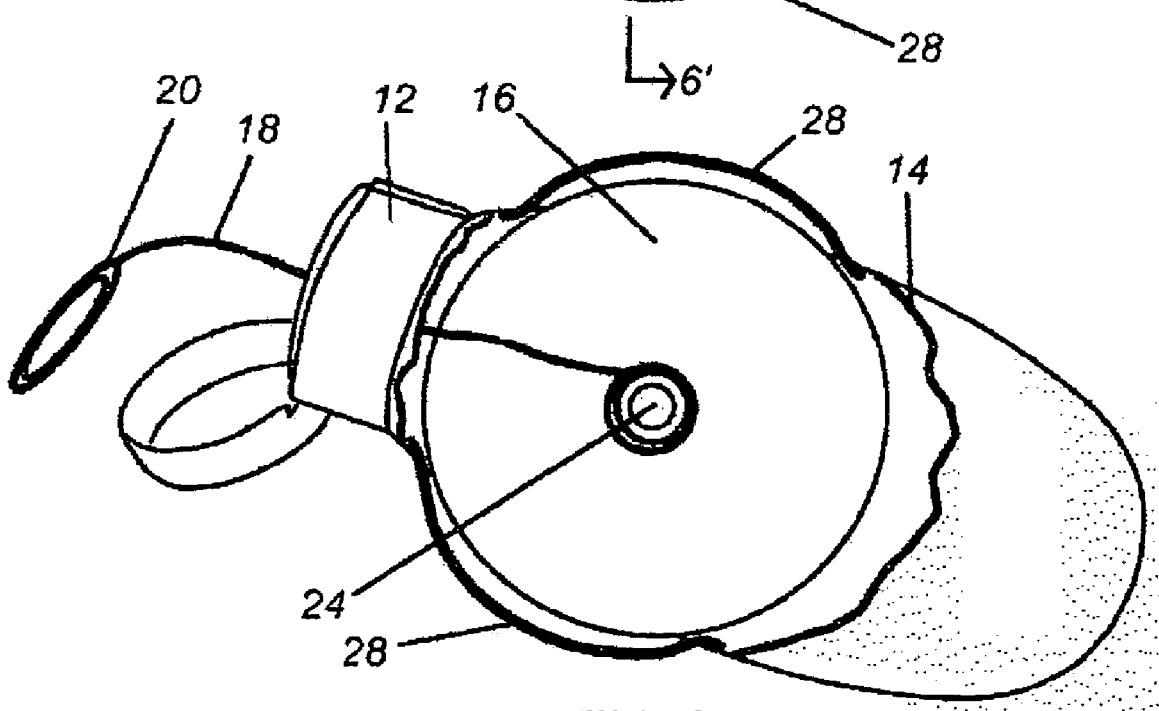
FIG. 4 is a cut away view of the present invention showing the disc with cable wound about the axle.

FIG. 4 illustrates a partial sectional view of the present invention with a portion of the container 14 body removed showing the disc 16 and those portions of the disc extending through slots in the body of the container covered by a flexible sheath, and the axle 24 about which the cable 18 is wound. The disc and axle are unitary and turning the disc manually rotates the axle. Preferably, the disc is turned by the thumb and forefinger as shown in FIG. 2 by pressing down through the flexible sheath covering those portions of the disc extending through the body of the container 14.

FIG. 5 illustrates a cut-away view taken along lines 6'-6' showing one embodiment of the present invention with having a flexible sheath 28 over those portions of the disc 16 that extend beyond the surface of the container 14. The sheath serves to prevent leakage of the contents of the container. Shown also are the axle retainers 26 formed in the container body for the retention of the unitary disc and axle allowing the axle to freely rotate.

FIG. 6 illustrates a cut-away view taken along lines 6'-6' showing another embodiment of the present invention with having a flexible seals 30 at the junction of the disc 16 and apertures serving to prevent leakage of the contents of the container. Although the seals are shown just below the surface of the container, they may be integrated into the container body itself at that point of intersection with the disc.

The sheath and seals may be combined in the construction of the present invention or separately to prevent leakage of container contents. The container body may be constructed of injection molded plastic or other suitable molding process in two parts and then fused together after insertion of the disc and pre-wound axle. A conventional lotion container cap with an annular orifice of adequate diameter such as to partially restrict the cable and remove excess lotion may be used, or the cap element may be part of the injection molded container body.

While the invention has been described in connection with only two embodiments of alternate sealing configurations, it is not intended to limit the scope of the invention to the particular form set forth, but on the contrary, it is intended to cover such alternatives, modifications, and equivalents as may be included within the spirit and scope of the invention as defined by the appended claims.

I claim:

1. A device for the self application of a fluid to the human body comprising:
   a fluid filled container body having a cavity, and opening, and, at least one apertures; and, a pair of axle retainers transversely formed into said cavity; and,
   a cap detachably affixed to said opening having an annular orifice therethrough into said cavity; and,
   a rotatable unitary disc and axle, medially positioned wherein the disc portion is aligned longitudinally relative to said container body, a portion of said disc extending through said at least one apertures of said container body; and wherein distal ends of said axle are supported by said axle retainers; and,
   a cable of adsorbent material connecting at the proximal end to, and wound about said axle, the distal end of cable extending through said orifice, and connected to a tab of larger diameter than said annular orifice preventing the cable from being fully retracted into said cavity.

2. The device of claim 1, wherein said portion of said disc extending through said at least one slot is loosely encapsulated by a flexible bladder for the retention of internal fluid.

3. The device of claim 1, having a plurality of flexible seals disposed between the junction of said unitary disc and said at least one apertures for the prevention of leakage of container contents.

4. The device of claim 1, wherein said container body having a single apertures through which a portion of said disc extends.

5. The device of claim 1, wherein said axle retainers further comprise molded indentations for the retention of the axle ends.

6. The device of claim 1, wherein said container is pre-filled with fluid.

7. A device for the measured application of a fluid to the human body comprising:
   a fluid filled container having an opening and at least one longitudinal slot; and,
   a disc with axle disposed within said fluid filled container, a portion of said disc extending through said at least one longitudinal slot and,
   a flip-top lotion cap having an annular orifice opening into a cavity of said container and situated over said opening; and,
   an adsorbent cable connected to and wound about said axle extending through said annular orifice, said adsorbent cable having a tab affixed at the distal end thereof; and,
   a pair of axle retainers formed transversely in said container for the retention of distal ends of said axle.

8. The device of claim 7, further comprising:
   a flexible sheath residing over that portion of said disc extending beyond a surface of said container, said flexible sheath preventing leakage of any contents within said container.

9. A device for the measured application of a fluid to the human body comprising:
   a fluid filled container having an opening and at least one longitudinal slot and,
   a unitary disc with axle disposed within said fluid filled container in which a portion of said disc extends through said at least one longitudinal slot in the container ; and,
   a flip-top lotion cap having an annular orifice opening into a cavity of said container and situated over said opening; and,
   an adsorbent cable connected to and wound about said axle extending though said annular orifice, said adsorbent cable having a tab affixed at the distal end thereof; and,
   a pair of axle retainers transversely formed in the body of said container for the rotatable retention of the unitary disc and axle.

10. The device of claim 9, further comprising:
    a flexible sheath residing over that portion of said disc extending through said at least one longitudinal slot for prevention of leakage of any contents within said container.

11. The device of claim 9, further comprising:
    a plurality of flexible seals disposed between the junction of said portion of disc and said at least one slot for the prevention of leakage of container contents.

* * * * *